US00PP12335P2

(12) United States Plant Patent
Heims

(10) Patent No.: US PP12,335 P2
(45) Date of Patent: Jan. 8, 2002

(54) TIARELLA PLANT NAMED 'CROW FEATHER'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/614,705

(22) Filed: Jul. 12, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette Para
(74) *Attorney, Agent, or Firm*—Klarquist Sparkman, LLP

(57) ABSTRACT

A new and distinct hybrid of Tiarella plant characterized by a unique combination of leaf shape and markings.

1 Drawing Sheet

The present invention relates to a new and distinct hybrid of Tiarella, of the family Saxifragaceae, which originated as a cross between an unpatented hybrid Tiarella named 'Pinwheel' (seed parent) and an unpatented, un-named hybrid tiarella with the Terra Nova designation '97-8' (pollen patent). Due to the fact that the instant plant and parent plants are the result of crosses between several different Tiarella species, no species designations are given.

This new Tiarella is a result of a controlled cross of the aformentioned plants at Terra Nova Nurseries, Inc., In Canby, Oreg. This hybrid was selected from a large selection of seedlings. Seed and pollen parent plants were retained to observe habit and to compare with the instant plant. The new variety has been reproduced only by asexual propagation (division and tissue culture). Each of the progeny exhibits identical characteristics to the original plant.

This plant is characterized by the following:

1. Unusual leaf shape characterized by parted or divided overlapping segments.
2. Strong marking along the veins.

Asexual propagation by division and tissue culture as done in Canby, Oreg., shows that the foregoing characteristics and distinctions come true to form and are established and transmitted through succeeding propagations.

BRIEF DESCRIPTION OF THE DRAWING

The drawing shows Tiarella 'Crow Feather' in April in Canby, Oreg.

DETAILED PLANT DESCRIPTION

The following is a detailed description of the new Tiarella hybrid based on observations of two-year-old specimens growing in a one-gallon pot in a cool greenhouse in Canby, Oreg. The color descriptions are all based on The Royal Horticultural Society Colour Chart.

Plant:
- *Type.*—Herbaceous perennial.
- *Form.*—Basal clump.
- *Size.*—16–22 cm. tall and 57 cm wide.
- *Hardiness.*—USDA Zone 4–5.

Foliage:
- *Type.*—Simple or of 3 leaflets.
- *Shape.*—Palmate or ternate. Generally pentagonal, but sometimes rhomboidal or trapezoidal due to overlapping lower segments.

- *Length.*—to 11.5 cm.
- *Width.*—to 9.5 cm.
- *Petiole length.*—to 25 cm.
- *Margins.*—Parted into 3 segments or divided into 3 leaflets. Individual segments/leaflets are clefted and incised, crenate-dentate, and ciliate.
- *Apex.*—Acute.
- *Base.*—Truncate or rounded.
- *Leaf texture.*—Hirsute.
- *Petiole texture.*—Pubescent.
- *Leaf arrangement.*—Basal rosette.
- *Venation.*—Reticulate.

Flower bud:
- *Size.*—2 mm. wide and 1.5 mm deep.
- *Description.*—Downfacing, campanulate when opening, puberulent.

Flower:
- *Type.*—Complete, perfect.
- *Shape.*—Stellate.
- *Size.*—7–8 mm. wide and 3.5 mm. deep including the stamens.
- *Petal count.*—5.
- *Petal shape.*—Elliptic with a clawed base.
- *Petal size.*—3.5 mm. long and 1 mm. wide.
- *Sepal count.*—5 lobes.
- *Sepal type.*—Petaloid, divided almost to the base.
- *Calyx size.*—6.5 mm. wide and 1 mm. deep.
- *Ovary position.*—Superior.
- *Carpel number.*—2.
- *Pistil size.*—4 mm. long.
- *Stamen number.*—10, conspicuously exerted.
- *Filament size.*—4 mm. long.
- *Inflorescence type.*—Raceme.
- *Peduncle width.*—1.5–2 mm.
- *Peduncle texture.*—Puberulent.
- *Blooming height.*—30–35 cm.
- *Bloom period.*—March to May.
- *Fragrance.*—Slight fragrance.
- *Lastingness.*—5 to 8 days.

Fruit:
- *Type.*—Capsule of 2 unequal parts.
- *Fertility.*—Fertile.

Seed: Ovoid, 1.2 mm. long and 0.5 mm. wide, shiny.

Disease: Minor susceptibility to powdery mildew when grown under poor conditions observed. No other disease has been observed on plants grown in Canby, Oreg.

Color characteristics:

*Foliage.*—Spring/Summer: Upper surface— RHS 137A to 139A Green Group. Upper surface, along veins— RHS 187A Greyed-Purple Group to RHS 202A Black Group. Lower surface— RHS 191A-B Greyed-Green Group.

*Petiole.*—RHS 200C Brown Group.

*Flower.*—Petal — RHS 155D White Group. Sepal— Somewhat lighter than RHS 36D Red Group. Pistil— RHS 155D White Group. Filaments— RHS 155D White Group. Anther, undehisced— RHS 37B Red Group. Pollen— RHS 31A Orange-Red Group.

*Peduncle.*—RHS 152A to 144A Yellow-Green Group.

*Capsule.*—RHS 160C Greyed-Yellow Group.

*Seed.*—RHS 202A Black Group.

DESCRIPTION OF PARENT PLANTS

The instant plant resulted from a cross between Tiarella 'Pinwheel' and an unnamed Tiarella designated 97-8. Tiarella 'Pinwheel' was selected as a parent plant for its broad, cut leaves that overlap 5% of the leaflet's width. The instant plant differs from Tiarella 'Pinwheel' in having much darker coloration along the veins and a fuller, more upright habit. The instant plant differs from Tiarella 97-8, which showed superior coloration but lacked overlapping leaflets and a more upright habit.

I claim:

1. A new and distinct hybrid of Tiarella plant substantially as shown and described, characterized by a unique combination of unusual leaf shape and markings.

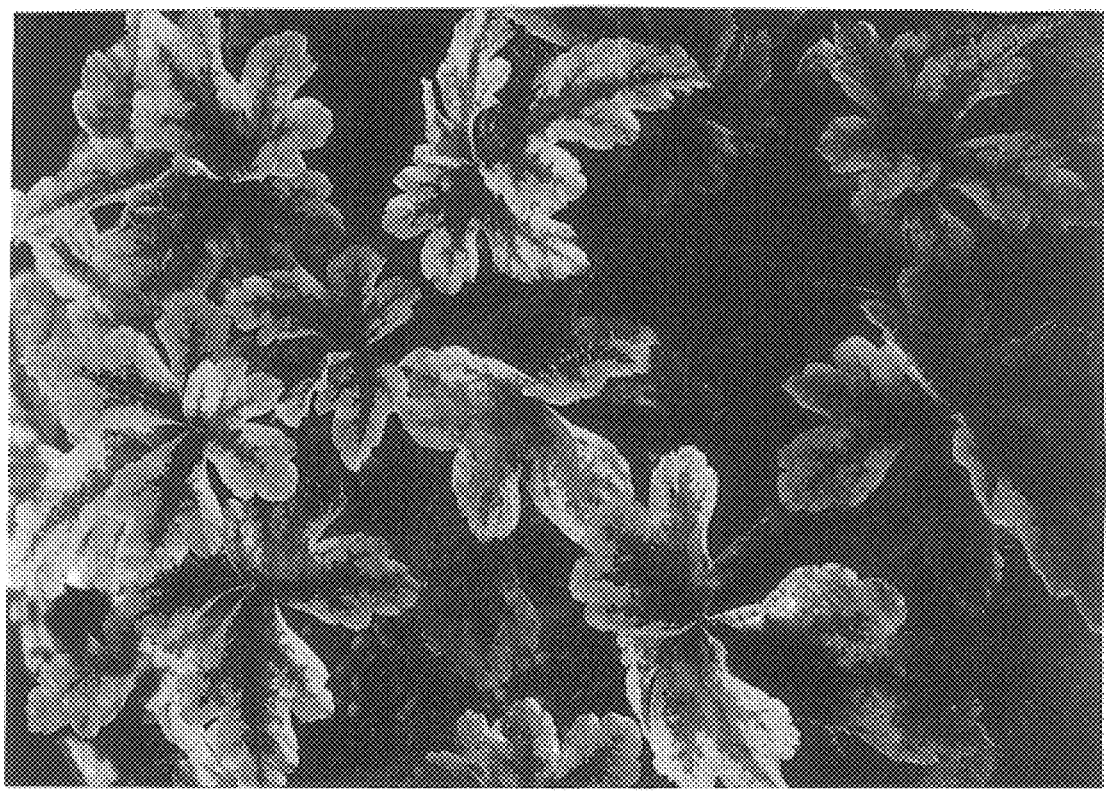

* * * * *